(12) United States Patent
Taylor

(10) Patent No.: US 7,452,206 B2
(45) Date of Patent: Nov. 18, 2008

(54) DENTAL CAST MODEL APPARATUS

(75) Inventor: Andrew Taylor, Sheffield (GB)

(73) Assignee: Neotek TDP Limited (GB)

( * ) Notice: Subject to any disclaimer, the term of this patent is extended or adjusted under 35 U.S.C. 154(b) by 257 days.

(21) Appl. No.: 11/133,052

(22) Filed: May 19, 2005

(65) Prior Publication Data

US 2005/0260537 A1 Nov. 24, 2005

(30) Foreign Application Priority Data

May 22, 2004 (GB) ................................ 0411451.8

(51) Int. Cl.
*A61C 13/00* (2006.01)
(52) U.S. Cl. ........................................ 433/34; 433/213
(58) Field of Classification Search ............... 433/34, 433/49, 60, 74, 213
See application file for complete search history.

(56) References Cited

U.S. PATENT DOCUMENTS

| | | | | |
|---|---|---|---|---|
| 3,436,827 A | * | 4/1969 | Dew | 433/34 |
| 3,702,027 A | * | 11/1972 | Marshall et al. | 433/34 |
| 4,283,173 A | * | 8/1981 | Browne et al. | 433/34 |
| 4,481,162 A | | 11/1984 | Huffman | |
| 4,538,987 A | * | 9/1985 | Weissman | 433/60 |
| 4,608,016 A | | 8/1986 | Zeiser | |
| 4,708,648 A | * | 11/1987 | Weissman | 433/49 |
| 5,306,145 A | * | 4/1994 | Michael | 433/34 |
| 5,506,095 A | * | 4/1996 | Callne | 433/34 |
| 6,019,601 A | * | 2/2000 | Cho | 433/60 |
| 6,149,428 A | * | 11/2000 | Mogensen | 433/74 |
| 6,425,759 B1 | * | 7/2002 | Cronin | 433/34 |
| 6,439,884 B1 | * | 8/2002 | Cronin | 433/34 |

FOREIGN PATENT DOCUMENTS

EP 1 097 678 A2 * 5/2001

* cited by examiner

*Primary Examiner*—Ralph A Lewis
(74) *Attorney, Agent, or Firm*—McKee, Voorhees & Sease, P.L.C.

(57) ABSTRACT

A dental cast model apparatus for the production and manipulation of dental model casts. The apparatus includes a model base having a mould adapted to produce a dental model. The model base is capable of supporting the dental model when formed and the model base is provided with one or more portions through or via which a force may be applied to said dental model when formed to remove said dental model from the model base.

13 Claims, 6 Drawing Sheets

DENTAL CAST MODEL APPARATUS

FIELD OF THE INVENTION

The present invention relates to dental cast model apparatus including bases or trays and models cast in such a base or tray, and in particular, but not exclusively, dental models which are used in the dental profession in the fabrication of dental restorations. Model base moulds for dental models allow the dental model contained within to be removed, sectioned and subsequently re-assembled as required.

BACKGROUND OF THE INVENTION

As the model bases allow for easy removal of individual sections of the dental model, lack of stability of the sections can occur which can seriously affect the accuracy of restorations. Pending European patent application EP 1097678 of the same inventor addresses this issue by utilising an A-frame within the mould to allow pins to extend through the mould and secure the dental model thereto.

In use, material is poured into the mould and solidifies to form the dental model. Suitable materials for pouring into the mould are plaster or artificial stone. A typical material for the dental model is α-hemihydrate of calcium sulphate. Preferably, the material has a hardness range which allows cutting thereof during sectioning of the model cast.

A problem with known moulds is that to remove the dental model from the mould, a high force is frequently required to overcome the adherence between the mould and the dental model, and a hammer is typically used to strike the mould. This can often result in undesirable damage to the dental model, especially if the hammer is caused to contact the model by mistake.

In addition a dental model is required to be cut into sections so that work can be carried out on each individual section. Repositioning of the individual sections within the mould can adversely result in misalignment, especially in the case that some damage has occurred during ejection of the model from the mould.

The aim of the present invention is to provide a model base which is of improved form and allows the improved removal of the dental model from the mould.

BRIEF SUMMARY OF THE INVENTION

According to a first aspect of the present invention, there is provided a dental cast model apparatus for the production and manipulation of dental model casts, the apparatus including a model base having a mould adapted to produce a dental model, wherein the model base is capable of supporting said dental model when formed and characterised in that the model base is provided with one or more portions through or via which a force may be applied to said dental model when formed to remove said dental model from said model base.

In one embodiment, a blanking plate is provided to engage the model base, said blanking plate provided with protrusions which cover the portions of the model base. When material which is to form the dental model is poured into the mould, the blanking plate prevents the material from leaking through the portions, when the blanking plate engages the model base.

According to a preferred embodiment, the portions of the model base are apertures. The apertures may be shaped to expose an area of the dental model when positioned in the model base, such that a force can be applied to said exposed areas through said apertures in order to eject the model from the base.

In an alternative embodiment, the portions are, or are covered by, a malleable and/or elastic material such as rubber, such that force may be applied to the dental model to eject the same via the malleable and/or elastic material, which stretches accordingly in response to the force and returns or can be returned to its original shape when the force is removed. A blanking plate is therefore not required in this embodiment.

Preferably the model base is recessed such that when the blanking plate fully engages the model base, the exterior surface of the blanking plate is flush with the surface of the model base. In one embodiment, the blanking plate forms a liquid seal with the model base when engaged.

The model base may be attached to an articulator which simulates a patient's jaw movements, thereby allowing the user to diagnose and plan treatment for the patient to which the dental model relates.

Preferably the model base is provided with articulator locating means to allow the model base to be fitted to an articulator. Preferably the articulator locating means are in the form of one or more openings.

Preferably the blanking plate can engage with the articulator locating means of the model base. Preferably the blanking plate locating means are in the form of one or more protrusions.

Preferably the blanking plate may be disengaged from the model base by applying force to the blanking plate locating means which may extend through the model base.

Preferably the blanking plate protrusions include any or any combination of numerals, letters and/or the like which may form an imprint on the dental model when the blanking plate engages the model base containing unhardened material. As the dental models formed are often sectioned, the imprinted characters aid the user in locating sections of the dental model during reconstruction of the same.

Preferably the blanking plate is also fitted with articulator locating means to allow the model base engaged with blanking plate to be fitted to an articulator. Preferably the blanking plate articulator locating means are in the form of one or more recesses.

Preferably the blanking plate is made of a non-friable material such as plastic. This helps prevent damage caused by the articulator to the model base and dental model therein.

Preferably the model base is provided with removable securing means which pass through and secure the dental model to the model base.

Preferably the removable securing means are in the form of removable sleeves which extend between surfaces of the mould, and removable pins which extend through the sleeves and ports in the model base.

The positions of the sleeves in the model base are thereby maintained by the pins passing through the same. The provision of pins in this manner is particularly advantageous in that, once the dental model has been formed, it is removed from the base and cut into multiple sections. The individual sections are then repositioned in the base so as to reform the complete dental model and individual sections can be removed, inspected and/or worked upon and subsequently returned to their correct position within the base. The pin therefore provides an indication that all the sections have bee correctly repositioned in the base, since any misalignment will prevent the pin passing all the way through the model. Thus it will be evident to anyone working on the model which section is misaligned due to the pin abutting that section, such that the section can be easily identified and repositioned as necessary.

Preferably the sleeves extend between vertical surfaces of the mould, and further preferably are in a parallel spaced relationship with the base of the mould.

Typically the sleeves are hollow structures to allow the insertion of the pins. According to a preferred embodiment, the sleeves include interior ribs or lobes which project radially inwardly to provide close fitting engagement with the pins inserted therein.

Preferably the sleeves and/or pins have a substantially constant diameter to facilitate the close fitting engagement therebetween. Preferably each pin has a handle section at one end thereof to assist insertion and/or removal of the same.

Preferably each pin can be inserted into the sleeve from either end of the sleeve, via an appropriate port in the model base, thereby avoiding conflicts with articulator and other components.

Preferably the rim of the model base includes one or more recesses or protrusions for improving the friction fit between the same and the dental model. Two or more sets of recesses or protrusions may be provided and one set of recesses/protrusions may be of different dimensions to a further set or protrusions/recesses so as to improve the keying of the dental model in the base.

In a further embodiment, an ejector plate is provided to engage the model base, said ejector plate provided with one or more protrusions which pass through the portions of the model base. Preferably the protrusions are arranged for the application of a force to the dental model at two or more discrete locations.

The ejector plate fits the model base, such that the protrusions force the dental model from the model base as the fit is tightened.

Preferably, the ejector plate is provided with locating means. Preferably the locating means arc in the form of a screw thread which may align with the model base articulator locating means when the ejector plate engages the model base. Preferably, an ejector handle is provided with tightening means. Preferably the tightening means are in the form of a screw thread complementary to the screw thread of the ejector plate locating means.

According to one particular embodiment, the locating means are in the form of a threaded recess within the ejector plate and the ejector handle is provided with tightening means in the form of a protruding threaded portion such that the ejector handle can be screwed into the ejector plate. Alternatively, the ejector plate locating means may be the male threaded portion which is received in a female portion within the ejector handle.

Thus, when the ejector plate engages the model bases either the locating means or the tightening means protrude through the model base to allow engagement between the ejector plate and the ejector handle. The tightening means may then be actuated to tighten the fit between the ejector plate and the model base, thereby ejecting the dental model from the model base as hereinbefore described.

According to a second aspect of the present invention, there is provided a dental cast model base for the production of dental model casts, the model base having a mould adapted to produce a dental model, wherein the model base is capable of supporting said dental model when formed and characterised in that the model base is provided with one or more portions through or via which a force may be applied to said dental model when formed to remove said dental model from said model base.

According to a third aspect of the present invention, there is provided a blanking plate for a dental model base, the model base being provided with one or more apertures arranged to expose an area of a dental model when formed, said blanking plate being shaped to engage with said dental model so as to seal said one or more apertures during formation of the dental model.

According to a further aspect of the present invention, there is provided an ejector plate for removing a dental model from a dental model base, said ejector plate being arranged for engagement with said model base and shaped such that a force applied to said ejector plate is transferred to one or more locations on the dental model through or via one or more corresponding portions on the model base.

BRIEF DESCRIPTION OF THE DRAWINGS

An embodiment of the invention will now be described, by way of example, with reference to the accompanying drawings, in which:—

DETAILED DESCRIPTION OF THE PREFERRED EMBODIMENT

Figure 1:
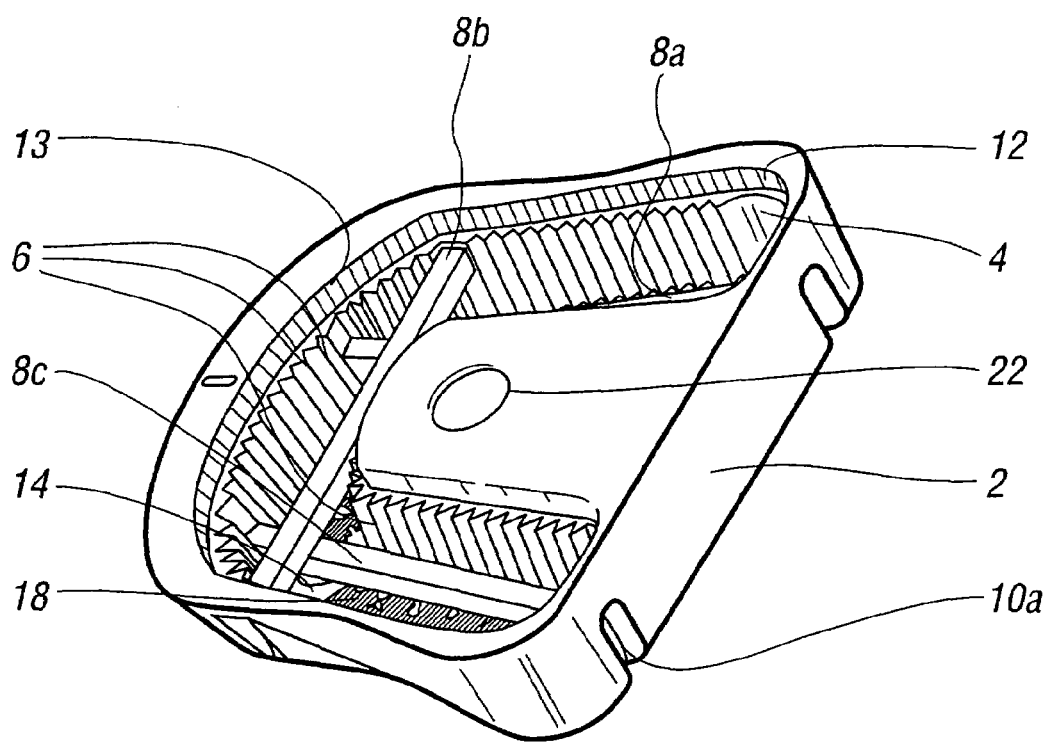
FIG. 1 shows a perspective view of a model base, with a mould and retaining means in accordance with one embodiment of the present invention.
Figure 2:
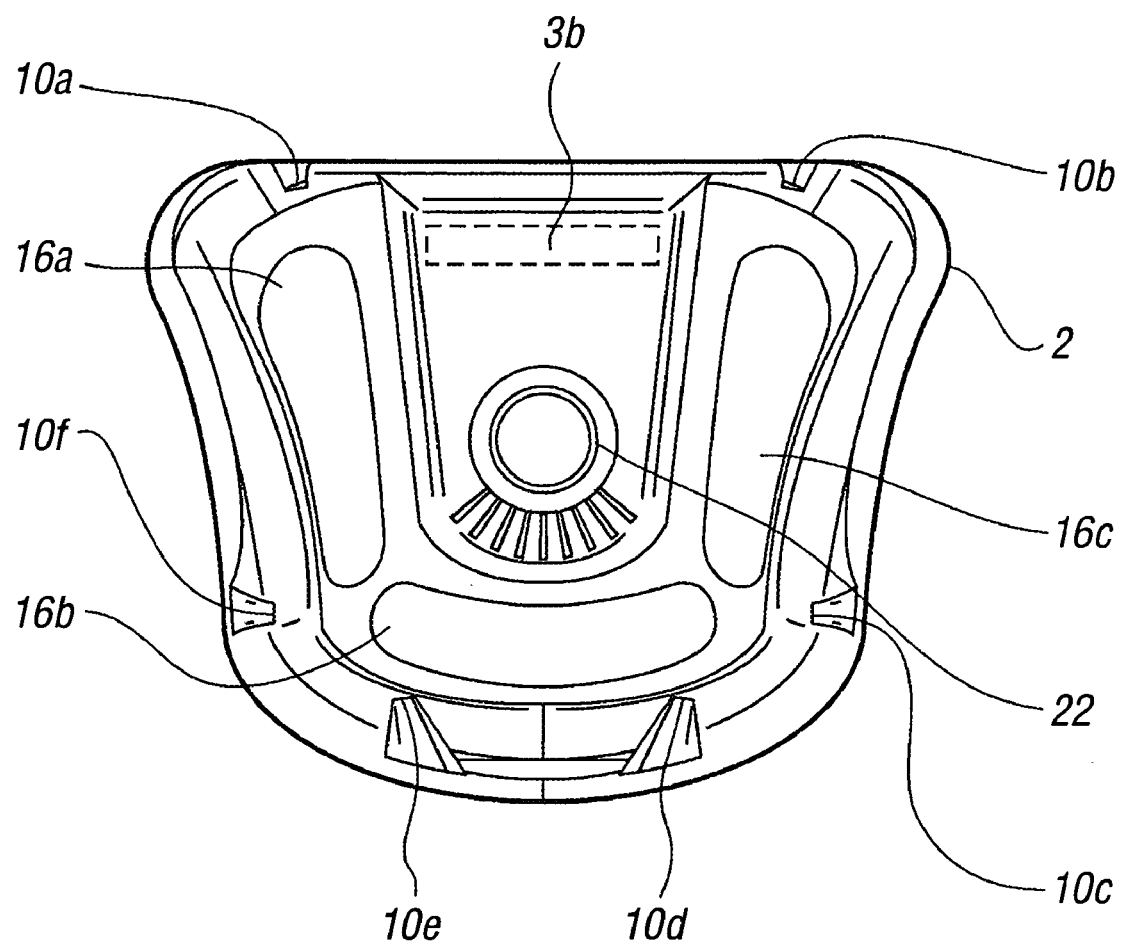
FIG. 2 shows a plan view of the model base, viewed from below.

Referring to FIGS. 1-2, there is indicated a model base 2 with a mould 4 formed in a "U" shaped manner so as to be capable of moulding an upper or lower impression of a patient's dentition. Material is poured into the mould 4, and the material hardens in the mould to form the dental model.

The model base 2 includes an articulator locating means in the form of an aperture 22 and a recess 30 to allow the same to be fitted to an articulator (not shown).

A plurality of vertical grooves 6 are provided on the inner and outer side walls of the mould 4, to aid in locating the dental model or sections thereof when removed and reinserted into the mould. The vertical grooves 6 located on the outer edge of the mould 4 are wider at the posterior of the mould 4 than at the anterior of the mould 4. The grooves 6 located on the inner edge of the mould 4 are all approximately the same width.

The differences in the widths of the vertical grooves 6 aid a user in locating a section of a dental model if reconstructed in the model base 2.

The model base 2 may be provided with an upper rim 12 which improves the location between the dental model and the model base 2, thereby aiding securement of the same. The upper rim may include a series of ridges or grooves 13 which are smaller than the grooves 6 on the outer edge and the posterior of the mould 4 so as to improve the keying of a dental model within the mould. Other combinations of grooves can be imagined, and the device is not limited to the example indicated.

Removable securing means are provided in the form of removable sleeves 8a-c which extend between surfaces of the mould 4. Together, the removable sleeves 8a-c form an A-frame.

Figure 3:
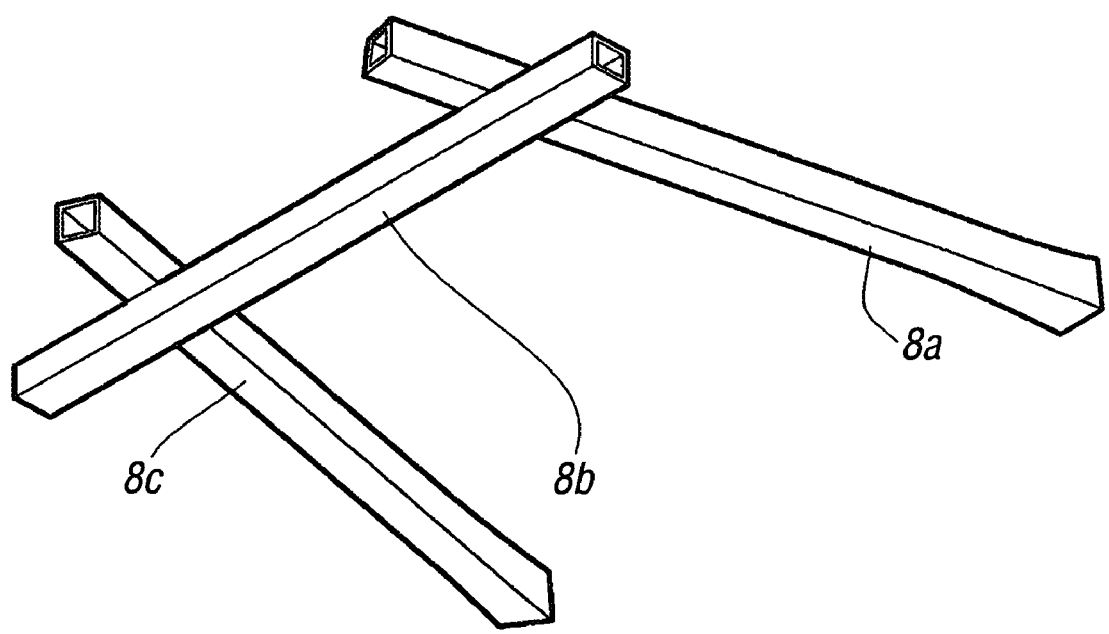
FIG. 3 shows a perspective view of the retaining means.

FIG. 3 shows the A-frame in more detail. The openings at the ends of the removable sleeves 8a-c line up with ports 10a-f in the model base 2, and a passage runs through each removable sleeve 8a-c to connect the openings at the ends of each removable sleeve 8a-c. Removable pins (not shown) may be provided which extend through the ports in the model base 2 and through the removable sleeves 8a-c, such that the removable sleeves 8a-c are positioned between the upper rim 12 of the model base 2 and the lower surface 14 of the mould 4.

Figure 4A:
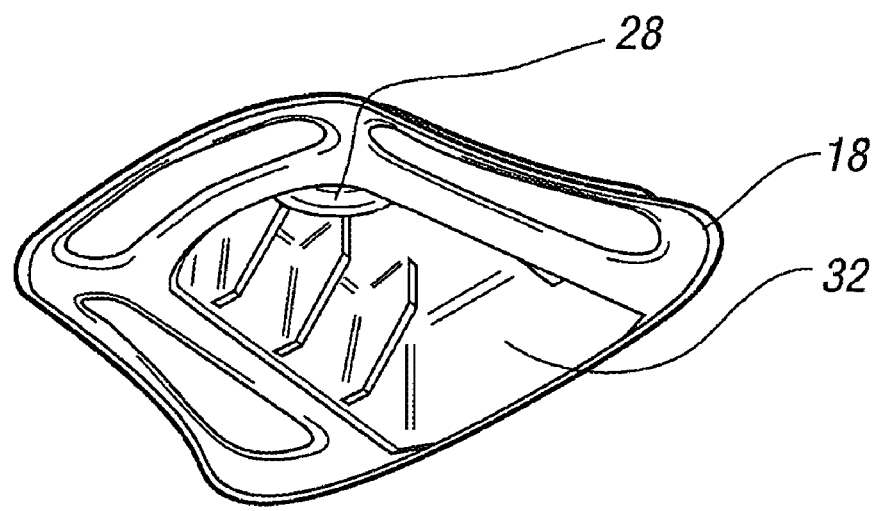
FIG. 4 shows a perspective view of the blanking plate (a) from below (b) from above.
Figure 4B:
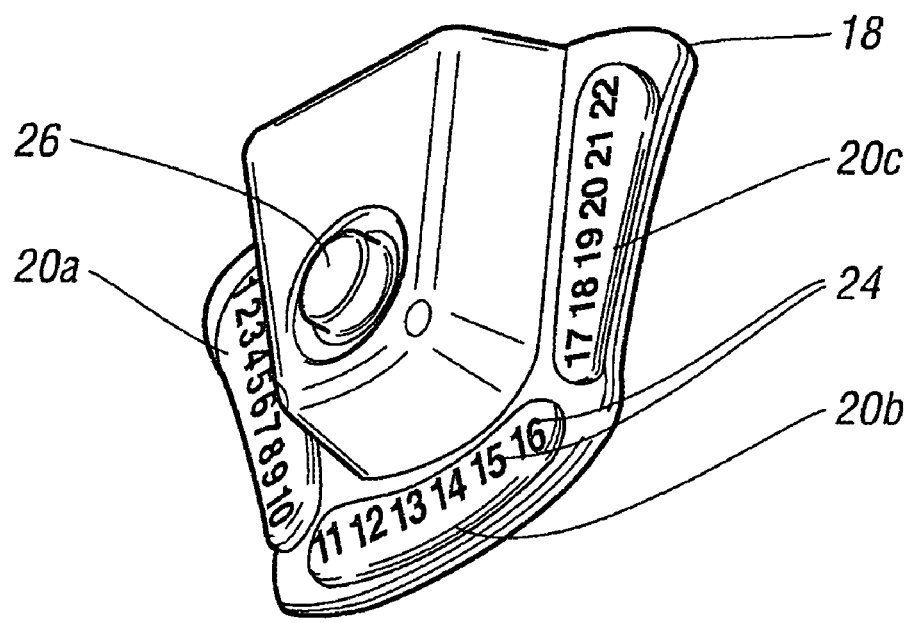

The lower surface 14 of the model base 2 is provided with portions which take the form of openings 16a-c, and a blanking plate 18, as shown in FIGS. 4a-b, may be fitted to the underside of the model base 2 as shown in FIG. 1. The blanking plate 18 in this embodiment includes protrusions 20a-c which fit into the respective openings 16a-c, and prevents liquid material from leaking from the mould 4 whilst a dental model is being formed. The protrusions 20a-c may be provided with numerals 24 or other markings to allow the dental model to be imprinted with the same.

When the material has hardened in the mould, the dental model may be removed from the mould 4 by removing the blanking plate 18 from the model base 2 and applying a force to the dental model through the openings 16a-c.

The blanking plate 18 includes a recess 32, and blanking plate locating means in the form of an extruded protrusion 26 of which the underside forms articulator locating means as a recess 28, such that model base 2 and blanking plate 18 together can be fitted to an articulator.

The blanking plate 18 is made of a non-friable material such as plastic, and forms the interface between the model base 2 and the articulator. Typically, the surface of the articulator to which the model base 2 and/or blanking plate 18 is fitted is also made of plastic. The model base 2 may be damaged by the action of the articulator if fitted directly to the same due to the brittle nature of the dental model material and the plastic fit of the articulator thereto. The blanking plate 18 reduces the risk of damage to the model base 2 caused by the action of the articulator is minimised due to the plastic-plastic fit.

Referring to FIGS. 5-6, there is indicated an ejector plate 36 which can be fitted to the underside of the model base 2 in a similar manner to that of the blanking plate 18. The ejector plate 36 is provided with protrusions 34a-c, the ends of which are raised above the lower surface 14 of the mould 4 when the ejector plate 36 is fully engaged with the model base 2. Thus a force applied to the ejector plate can be exerted to the underside of the dental model such that the model is displaced a short distance, dislodging the model from its seating within the base 2. In addition, any applied load is distributed over the area of the protrusions 34a-c. This avoids the application of a pressure sufficient to break the model and allows a more even force to be applied to the dental model to remove the same from the mould 4.

Figure 5A:
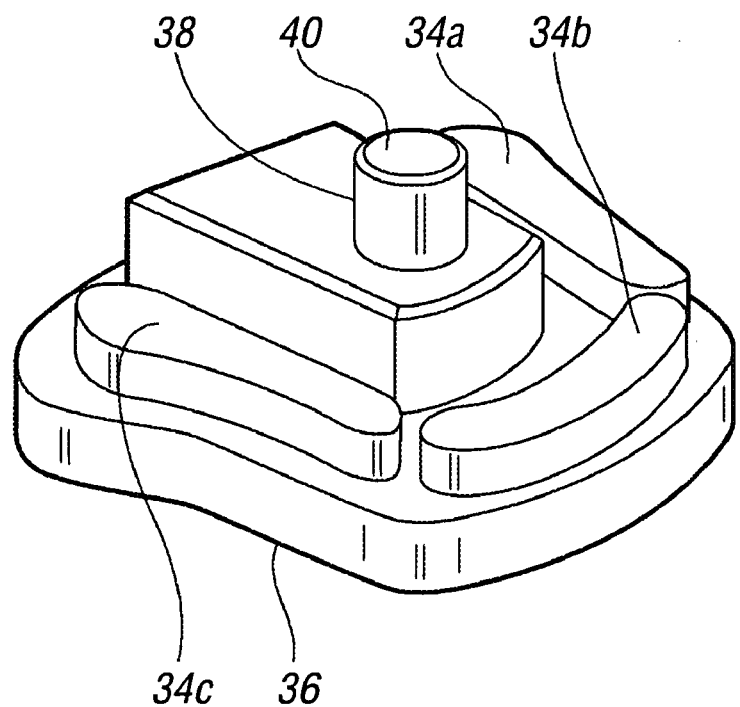
FIGS. 5a and b show a perspective view of the ejector plate according to two embodiments of the present invention.
Figure 5B:
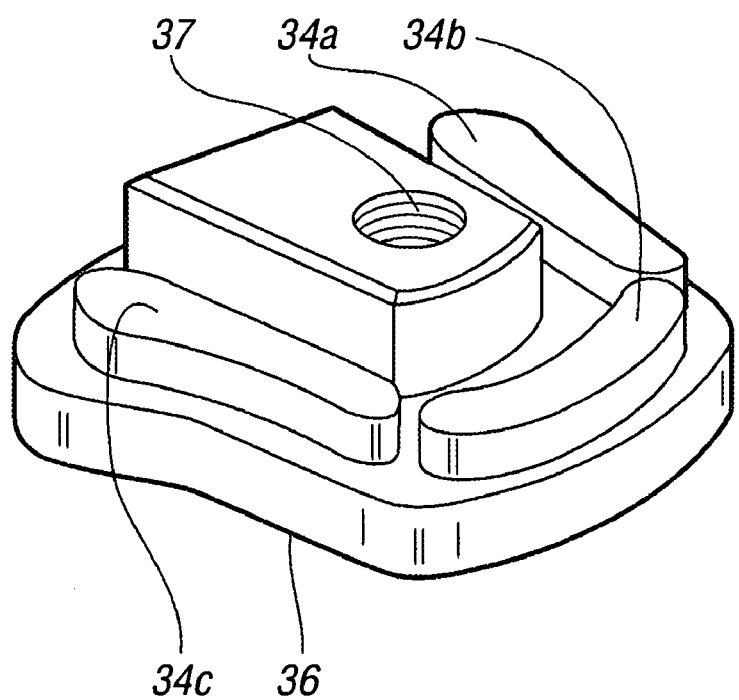

The ejector plate may also be provided with locating means as shown in FIGS. 5a and 5b. In FIG. 5a, the locating means takes the form of a protrusion 38 which passes through the aperture 22 in the model base 2. The protrusion 38 is provided with ejector plate locating means in the form of an external screw thread 40 to which a tool 42 in FIG. 6a can be fitted by way of a complementary internal screw thread 44.

Figure 6B:
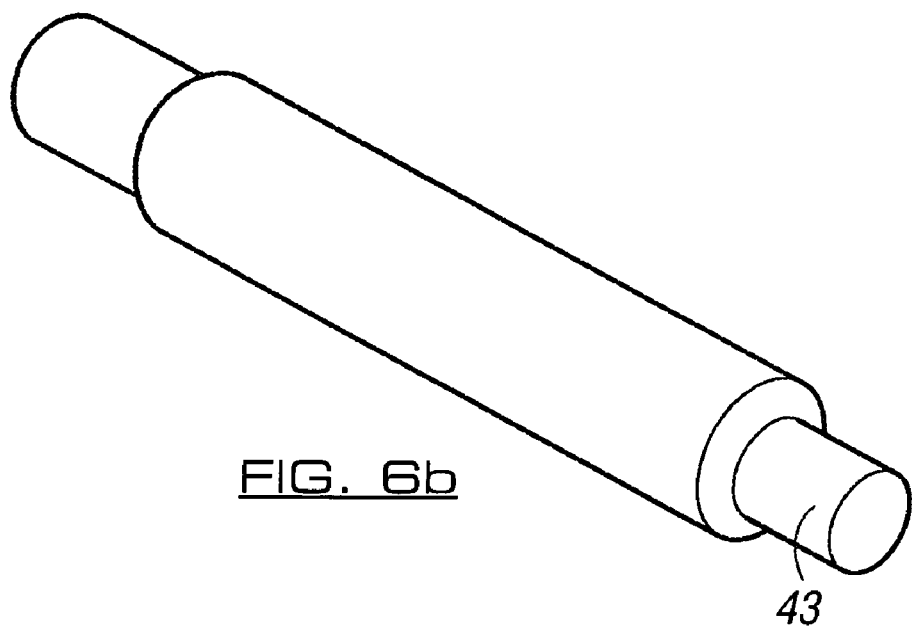
FIGS. 6a and b show a perspective view of the ejector handle according to two embodiments of the present invention.
Figure 6A:
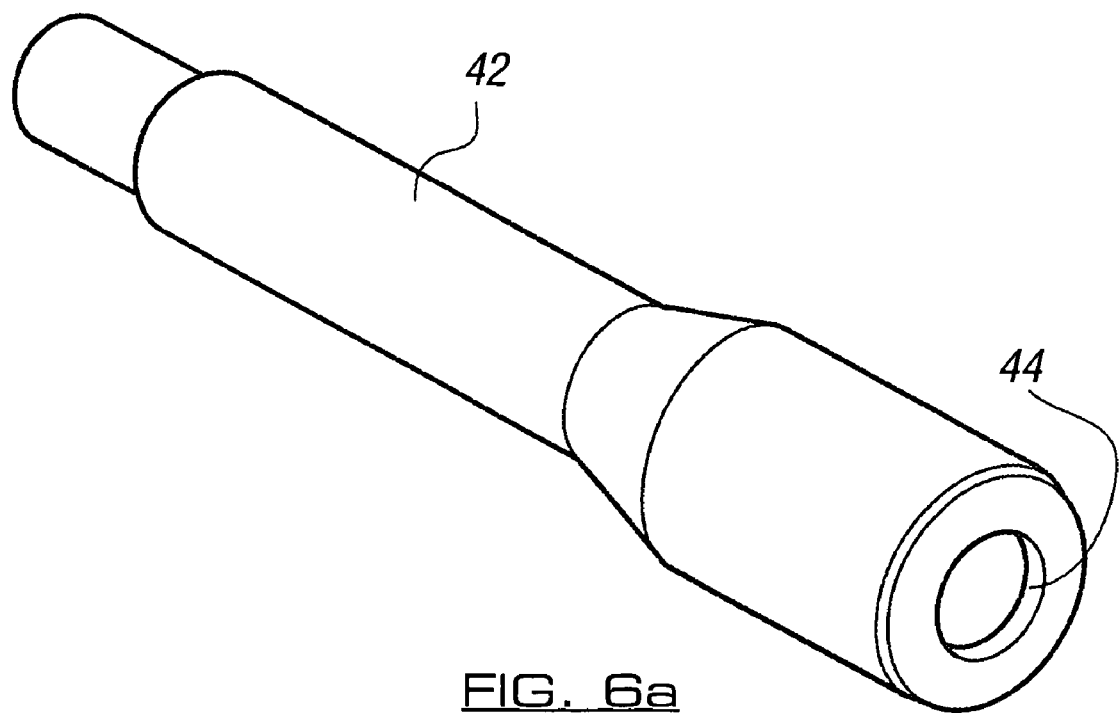

FIGS. 5b and 6b show an alternative embodiment which is in many ways preferred, wherein the locating means is a threaded aperture 37. In this embodiment, the tool 42 is provided with a threaded protrusion 43 which is received by the aperture 37 in the ejector plate.

With the ejector plate 36 in position with respect to the model base 2 and the tool 42 in position, actuation or rotation of the tool 42 causes the fit between the ejector plate 36 and the model base 2 to be tightened, causing the protrusions 34a-c to advance into the openings 8a-c such that the protrusions 34a-c eject the dental model from the mould 4. The tool allows force to be increased gradually and applied evenly to the dental model to minimise the stress applied thereto and avoid damage to the same.

The tool may be provided with any or any combination of grips, handles, levers, knobs, and the like to enable the user to actuate the tool more easily.

It will be appreciated by persons skilled in the art that the present invention also includes further additional modifications made to the device which does not effect the overall functioning of the device. In particular it has been found that the shape, size and number of openings in the base may be altered, as well as the contour of the inner and outer side walls of the mould in order to provide improved structural characteristics without departing from the scope of the appended set of claims.

What is claimed is:

1. A dental cast model apparatus for the production and manipulation of dental model casts, the apparatus including
   a model base having a mould adapted to produce a dental model, wherein the model base is capable of supporting said dental model when formed,
   and the model base is provided with one or more apertures through which a force may be applied to said dental model when formed to remove said dental model from said model base,
   said apparatus further including removable means which pass through the dental model for securing the dental model to the model base prior to removal of the dental model therefrom and
   wherein a blanking plate is also provided,
   said blanking plate including protrusions shaped to extend into said apertures of the model base when the blanking plate is engaged so as to close and seal said apertures during the formation of the model.

2. An apparatus according to claim 1, characterised in that a part of said dental model once formed is seated within the model base and the one or more apertures expose an area of the model within the base.

3. An apparatus according to claim 1, characterised in that the blanking plate protrusions are shaped to form an imprint on the dental model when the blanking plate is engaged with the model base containing unhardened material.

4. An apparatus according to claim 1, characterised in that the blanking plate is shaped to form a liquid seal with said model base when engaged.

5. An apparatus base according to claim 1, characterised in that the model base is provided with one or more openings to allow the model base to be fitted to an articulator.

6. An apparatus according to claim 1, characterised in that the model base has one or more inner surfaces with recesses and/or protrusions to ensure correct positioning of the dental model within the base.

7. An apparatus according to claim 6, characterised in that the recesses and/or protrusions are provided in sets,
   the dimensions of one or more sets being different from the dimensions of one or more further sets.

8. An apparatus according to claim 1, characterised in that an ejector plate is engageable with the model to remove said dental model from said model base.

9. An apparatus according to claim 8, characterised in that the ejector plate includes one or more protrusions arranged to locate with the one or more apertures of the model base.

10. An apparatus according to claim 9, characterised in that the ejector plate fits the model base such that the protrusions force the dental model from the model base as the fit is tightened.

11. An apparatus according to claim 8, characterised in that the ejector plate is provided with locating means.

12. An apparatus according to claim 11, characterised in that a tightening means is engageable with said locating means so as to tighten the engagement between the dental model and the model base.

13. An apparatus according to claim 12, characterised in that the locating means and/or tightening means are provided with a threaded portion.

* * * * *